(12) United States Patent
Flores et al.

(10) Patent No.: US 9,675,328 B2
(45) Date of Patent: Jun. 13, 2017

(54) CATHETER PATCH APPLICATOR ASSEMBLY

(75) Inventors: Jesus Flores, El Paso, TX (US); Scott Tufts, El Paso, TX (US)

(73) Assignee: CAREFUSION 2200, INC., San Diego, CA (US)

( * ) Notice: Subject to any disclaimer, the term of this patent is extended or adjusted under 35 U.S.C. 154(b) by 857 days.

(21) Appl. No.: 12/910,626

(22) Filed: Oct. 22, 2010

(65) Prior Publication Data

US 2012/0101482 A1   Apr. 26, 2012

(51) Int. Cl.
| A61B 17/00 | (2006.01) |
| A61B 17/08 | (2006.01) |
| A61F 15/00 | (2006.01) |
| A61M 25/02 | (2006.01) |

(52) U.S. Cl.
CPC ............ *A61B 17/00* (2013.01); *A61F 15/005* (2013.01); *A61M 2025/0273* (2013.01)

(58) Field of Classification Search
CPC .............. A61B 18/29; A61B 18/22031; A61B 18/2909; A61B 2017/22031
USPC ............. 606/1, 213–217, 205; 604/174–180, 604/288.01–288.04
See application file for complete search history.

(56) References Cited

U.S. PATENT DOCUMENTS

| 5,569,207 A | | 10/1996 | Gisselberg et al. |
| 5,631,322 A | | 5/1997 | Veronese et al. |
| 6,106,542 A | * | 8/2000 | Toybin et al. ................ 606/205 |
| 6,447,798 B1 | | 9/2002 | Munro et al. |
| 6,663,622 B1 | * | 12/2003 | Foley et al. .................... 606/34 |
| 6,683,120 B2 | | 1/2004 | Munro |
| 2003/0225422 A1 | * | 12/2003 | Mosnier et al. ............... 606/151 |
| 2005/0125013 A1 | * | 6/2005 | Kessler ........................ 606/148 |
| 2005/0267529 A1 | * | 12/2005 | Crockett et al. .............. 606/215 |
| 2006/0020288 A1 | * | 1/2006 | Leonard ........................ 606/205 |
| 2007/0244477 A1 | * | 10/2007 | Santilli ............. A61B 18/1442 606/29 |
| 2007/0299469 A1 | * | 12/2007 | Carpenter et al. ............ 606/205 |
| 2008/0064929 A1 | * | 3/2008 | Wiedenbein .................. 600/131 |
| 2008/0167680 A1 | * | 7/2008 | Voegele et al. ............... 606/206 |

(Continued)

OTHER PUBLICATIONS

Definition of "abut". Free Dictionary, retrieved Dec. 13, 2015; Retrieved from the internet: <http://www.thefreedictionary.com/abut>.*

(Continued)

*Primary Examiner* — Lynsey Crandall
*Assistant Examiner* — Sebastian X Lukjan
(74) *Attorney, Agent, or Firm* — Arent Fox LLP (57) ABSTRACT

In accordance with aspects of the present invention, an applicator assembly suitable for application of a catheter patch with one hand comprises an upper arm with a proximal end and a distal portion, a lower arm with a proximal end and a distal portion, and a hinge member fixedly joining the proximal ends of the upper arm and the lower arm, wherein an upper surface of the upper arm distal portion abuts a lower surface of the lower arm distal portion. In accordance with another aspect of the present invention, a catheter patch assembly may be secured against a lower surface of the upper arm distal portion. The distal portion of the lower arm may include a securing mechanism for securing the catheter patch assembly to the applicator assembly. A method of applying a catheter patch is provided.

25 Claims, 6 Drawing Sheets

(56) References Cited

U.S. PATENT DOCUMENTS

2008/0171993 A1\* 7/2008 Beran .......................... 604/180
2009/0082801 A1\* 3/2009 Giese et al. .................. 606/210
2012/0078293 A1\* 3/2012 Hassidov et al. ............. 606/213

OTHER PUBLICATIONS

Definition of "contact". Free Dictionary, retrieved Dec. 13, 2015; Retrieved from the internet: <http://www.thefreedictionary.com/contact>.\*

Definition of "extend". Merriam Webster, retrieved Dec. 17, 2015; Retrieved from the internet: <http://www.merriam-webster.com/dictionary/extend>.\*

Definition of "through". Merriam Webster, retrieved Dec. 18, 2015; Retrieved from the internet: <http://www.merriam-webster.com/dictionary/through>.\*

\* cited by examiner

CATHETER PATCH APPLICATOR ASSEMBLY

BACKGROUND

Field

The present disclosure relates to a catheter patch applicator assembly and method of use thereof, and more particularly, to a catheter patch applicator assembly that permits single-hand sterile application of a catheter patch to a patient's skin for lubricating catheters, as surgical dressings, and/or as wound dressings.

Description of Related Art

Surgical dressings, wound dressings, and catheter-securing patches for use with catheters or other percutaneous devices, such as feeding tubes, orthopedic fixation pins, or electrical leads, for example, are common in the prior art. The primary concern with transdermal access into the body is the prevention of infection and irritation to the insertion site of the percutaneous device.

For example, long-term care and vascular access catheters are increasingly used to provide indefinite access to a patient's blood vessels for drawing blood or administering medication. The placement of a catheter often relieves a patient of having to endure multiple sticks of a needle once an intravenous (IV) site is established and preserves the integrity of blood vessels, for example, by providing a single site for prolonged access to the patient's circulatory system. The significant increase in the use of long-term catheterization of patients, including in a wide array of settings, such as hospitals, nursing homes, and home health care, for example, creates even greater need for the prevention of irritation to the skin and microbial intrusion into the insertion site.

Each time a dressing is applied to stabilize or protect the insertion site, there exists an opportunity for foreign contamination of the insertion site via the fingers and hands of a technician or medical provider, for example. Long-term applications require repeated changing of the dressing around the percutaneous puncture site. Each time the dressing is changed, an opportunity arises for bacteria or some other foreign contaminant to infect or otherwise irritate the puncture or wound site.

Medical practitioners are trained persistently on the methods of sterile application of a dressing in order to lower the risk of infection or contamination to a percutaneous insertion site. Unfortunately, the manner in which dressings or patches of the related art are designed and/or applied often requires the use of both hands to hold and apply a dressing to a catheter site, or the placement of fingers near the insertion site to hold and/or apply the dressing or patch. This significantly increases the likelihood of contamination of a sterilized IV site or the sterilized patch itself by the hands and/or fingers.

There exists a need in the field for a catheter patch that permits the efficient application of the patch around percutaneous devices of varied sizes while helping keep the hands and/or fingers away from the insertion site.

SUMMARY

In accordance with aspects of the present invention, an applicator assembly suitable for application of a catheter patch with one hand comprises an upper arm with a proximal end and a distal portion, a lower arm with a proximal end and a distal portion, and a hinge member fixedly joining the proximal ends of the upper arm and the lower arm, wherein an upper surface of the upper arm distal portion abuts a lower surface of the lower arm distal portion.

In accordance with another aspect of the present invention, a catheter patch assembly may be secured against a lower surface of the upper arm distal portion.

In accordance with another aspect of the present invention, the distal portion of the lower arm has a securing mechanism for securing the catheter patch assembly to the applicator assembly. The securing mechanism may include retaining posts that extend from a lower surface of the upper arm distal portion.

In accordance with yet another aspect of the present invention, the upper arm and lower arm may respectively comprise upper and lower arm bridging portions, the upper and lower arm bridging portions configured to extend longitudinally from upper and lower arm base portions to the upper and lower arm distal portions along opposite sides of a vertical longitudinal centerline plane of the applicator assembly.

In accordance with yet another aspect of the present invention, a method of applying a catheter patch about an insertion site of a percutaneous device includes providing an applicator assembly comprising an upper arm and a lower arm cantilevered from a hinge member, the upper and lower arms each having distal portions, wherein the applicator assembly is configured with the distal portion of the upper arm positioned below the distal portion of the lower arm, and wherein a catheter patch assembly comprising a tacky layer is secured to the applicator assembly, exposing a lower surface of the tacky layer, positioning the percutaneous device within an aperture formed in the tacky layer via an access channel provided in the tacky layer, contacting the exposed lower surface of the tacky layer with the skin adjacent the percutaneous device insertion site, applying pressure to the upper arm to hold the tacky layer against the skin, and applying pressure to the lower arm in a direction toward the upper arm to displace the distal portion of the lower arm away from the distal portion of the upper arm and release the tacky layer from the applicator assembly.

It will become readily apparent to those skilled in the art from the following detailed description, wherein it is shown and described only exemplary configurations of a catheter patch and assembly. As will be realized, the invention includes other and different aspects of a catheter patch and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Various aspects of a catheter patch and applicator assembly may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of a catheter patch and applicator assembly in addition to the orientation depicted in the drawings. By way of example, if a catheter patch and applicator assembly in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of a catheter patch and applicator assembly may be illustrated with reference to one or more exemplary embodiments. As used herein, the term "exemplary" means "serving as an example, instance, or illustration," and should not necessarily be construed as preferred or advantageous over other embodiments of a catheter patch and applicator assembly disclosed herein.

Figure 1:
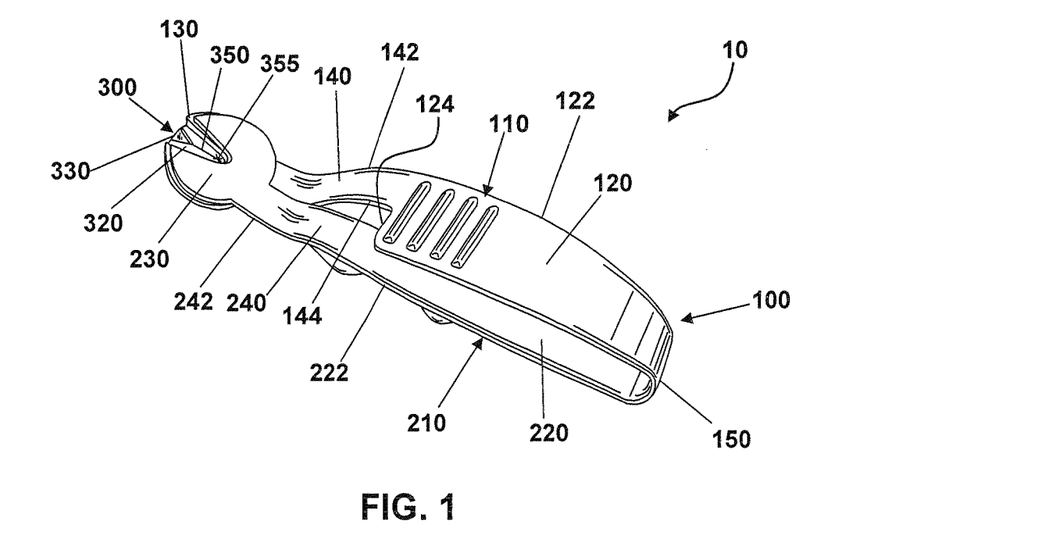
FIG. 1 is a top perspective view of a catheter patch and applicator assembly, in accordance with certain aspects of the present invention.
Figure 2:
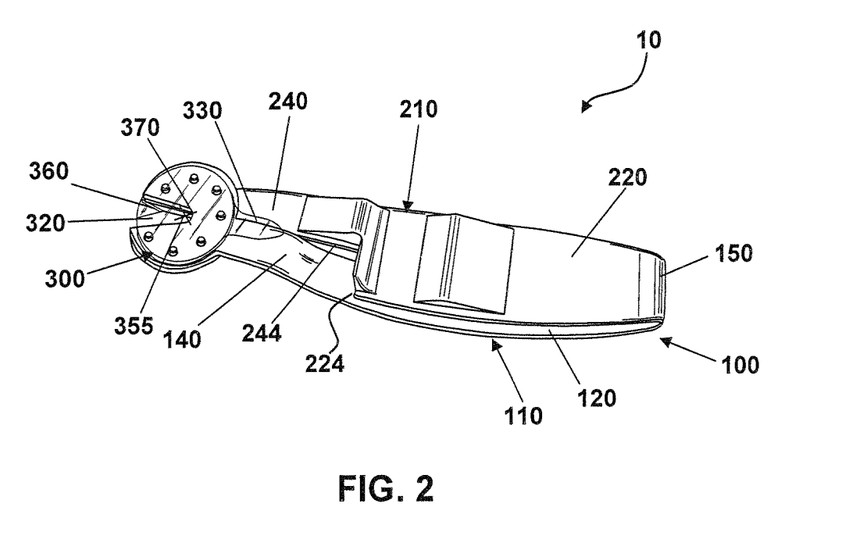
FIG. 2 is a bottom perspective view of the catheter patch and applicator assembly of FIG. 1, in accordance with certain aspects of the present invention.

The catheter patch and applicator assembly may be compact and ergonomically designed. As shown in FIGS. 1 and 2, the catheter patch and applicator assembly 10 may comprise an applicator assembly 100 and a catheter patch assembly 300 mounted thereto. The applicator assembly 100 comprises an upper arm 110 and a lower arm 210 fixedly hinged to each other by a hinge member 150 toward or at a proximal end of the applicator assembly 100. The upper arm 110 comprises a proximal base portion 120 connected to a distal portion 130 by a bridging portion 140, and the lower arm 210 similarly has a proximal base portion 220 connected to a distal portion 230 by a bridging portion 240. The catheter patch assembly 300 may be removably associated with the distal portion 130, 230 of the applicator assembly 100.

Figure 3:
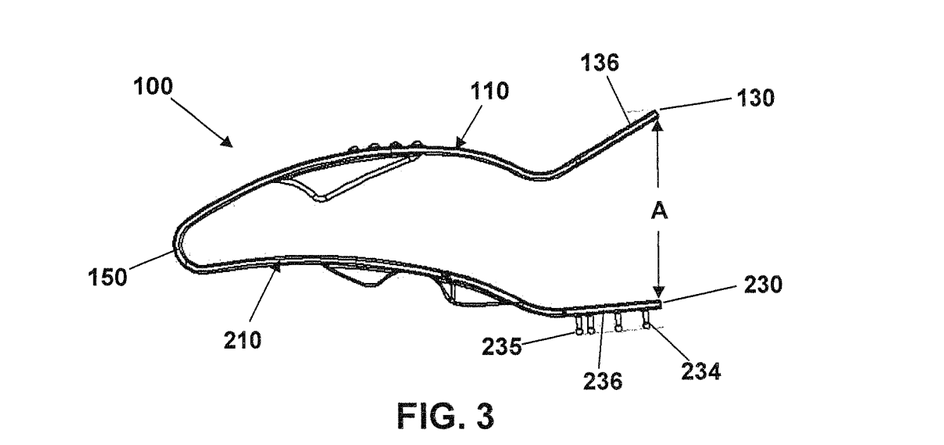
FIG. 3 is a side plan view of the applicator assembly of FIG. 1 in an initial configuration, in accordance with certain aspects of the present invention.

The applicator assembly 100 is preferably formed of a plastic material, such as high density polyethylene, or any suitable material exhibiting similar flexibility and integrity. Although any suitable hinge member 150 may be provided, the upper arm 110 and the lower arm 210 are preferably integrally formed and coupled at the proximal end with an arched hinge member 150. As shown in FIG. 3, for example, the applicator assembly 100 may be formed so that the upper arm 110 and the lower arm 210 extend in cantilever fashion from the hinge member 150. Thus, substantially opposing forces may be applied against distal points along each of the cantilevered arms 110 and 210 to direct the arms from an initial position, where the arms 110 and 210 are separated by a gap A, for example, toward one another. Similar to a pair of tongs, for example, the hinge member 150 acts as a spring, resisting the deflection of the upper and lower arms 110 and 210 and acting to force open the arms in an attempt to return the applicator assembly 100 to the initial position.

Figure 4:
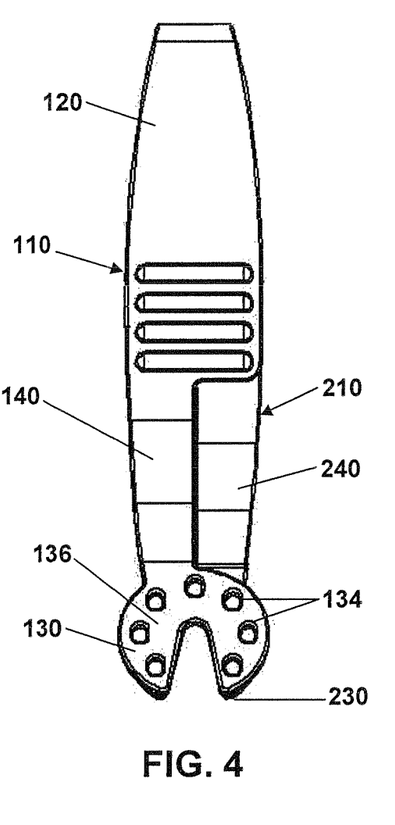
FIG. 4 is a top view of the applicator assembly of FIG. 3, in accordance with certain aspects of the present invention.

As shown in FIGS. 1 and 2, the bridging portion 140 of the upper arm 110 may be configured to extend longitudinally from substantially one side of the base portion 120 to connect to the distal portion 130. The bridging portion 140 may have an outer edge 142, providing a seamless continuation of a contoured outer edge 122 of the base portion 120, and a contoured inner edge 144, extending substantially along a vertical longitudinal centerline plane of the applicator assembly 100 from a lateral step 124 to the distal portion 130. Similarly, the bridging portion 240 of the lower arm 210 may be configured to extend longitudinally from substantially one side of the base portion 220 to the distal portion 230. The bridging portion 240 may have an outer edge 242, providing a seamless continuation of a contoured outer edge 222 of the base portion 220, and a contoured inner edge 244, extending substantially along a vertical longitudinal centerline plane of the applicator assembly 100 from a lateral step 224 to the distal portion 230. As shown in FIGS. 1, 2 and, in particular, FIG. 4, the bridging portions 140 and 240 extend along opposite sides of the vertical longitudinal centerline plane of the applicator assembly 100, so that when viewed from above or below, for example, the distal portions 130 and 230 align above and below one another, respectively.

Figure 5:
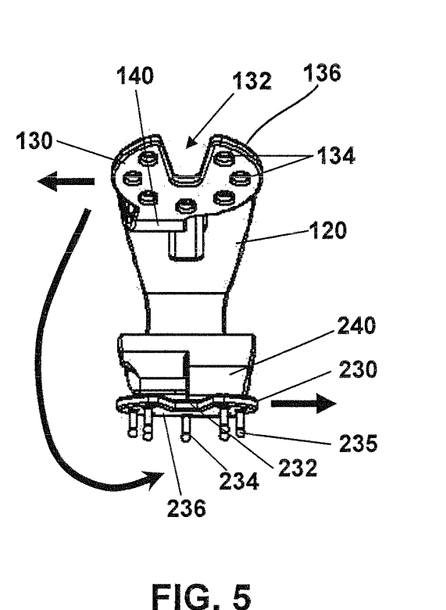
FIG. 5 is a front view of the applicator assembly of FIG. 3, in accordance with certain aspects of the present invention.
Figure 6:
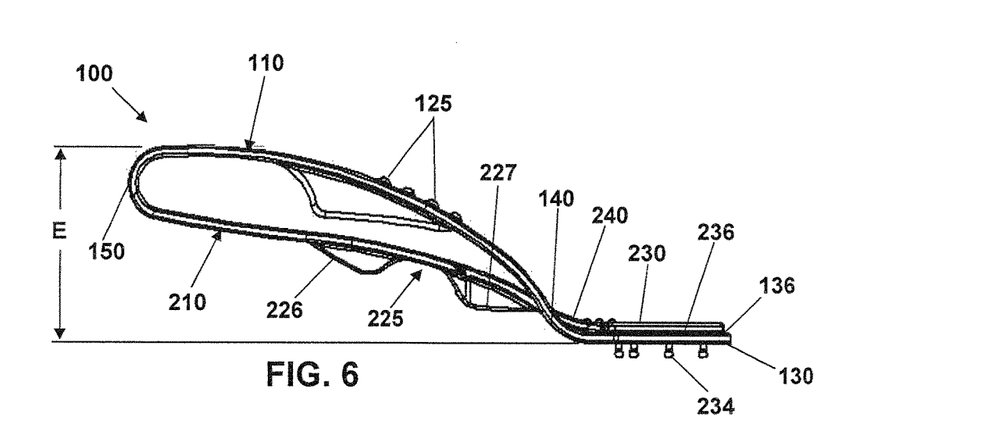
FIG. 6 is a side plan view of the applicator assembly of FIG. 1 in an assembled position, in accordance with certain aspects of the present invention.
Figure 7:
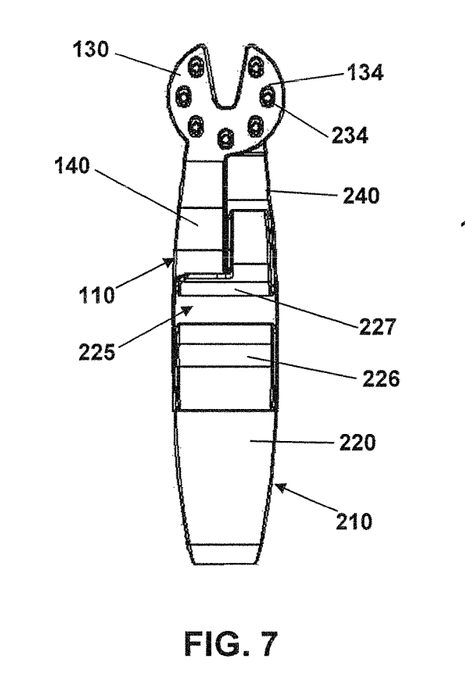
FIG. 7 is a bottom view of the applicator assembly of FIG. 6, in accordance with certain aspects of the present invention.
Figure 8:
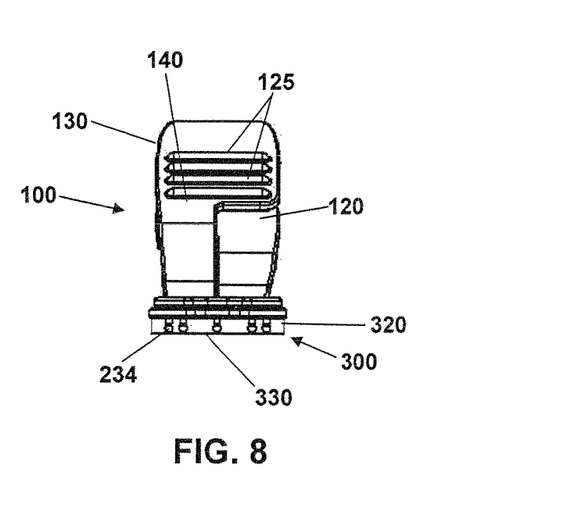
FIG. 8 is a front view of the applicator assembly of FIG. 6 with a catheter patch assembly mounted thereto, in accordance with certain aspects of the present invention.

As shown in FIG. 5, the distal portion 130 of the upper arm may be formed with a positioning notch 132 and one or more mounting apertures 134, and the distal portion 230 of the lower arm may be formed with a positioning notch 232 and one or more retaining posts 234. In assembling the combination of a catheter patch assembly 300 and an applicator assembly 10, the applicator assembly 100 may be prepared for receiving the catheter patch assembly 300 by sliding the distal portion 130 of the upper arm 110 under distal portion 230 of the lower arm 210 so that the one or more retaining posts 234 align with and extend through the one or more mounting apertures 134. Thus, as shown by the arrows in FIG. 5, in order to achieve the desired configuration for mounting the catheter patch assembly 300, the upper arm 110 and the lower arm 210 may be displaced laterally away from one another, keeping the respective bridging members 140 and 240 toward the outside of the applicator assembly 100. The upper arm 110 and the lower arm 210 may then be forced, against the resistance of the hinge member 150, to displace vertically toward one another, closing the gap A so that the distal portion 130 may pass laterally to a side of the distal portion 230. Once below the level of the retaining posts 234, the distal portion 130 may be positioned under the distal portion 230. Thus, as shown in FIGS. 6-8, the natural inclination of the compressed hinge member 150 to force the arms 110 and 210 back into an open position forces an upper surface 136 of the distal portion 130 to seat against a lower surface 236 of the distal portion 230, wherein the one or more retaining posts 234 extend through the one or more mounting apertures 134, and the positioning notches 232 and 132 are in substantial alignment. In this position, the applicator assembly 100 is essentially locked in a secure configuration by the vertically applied spring force of the hinge member 150 in combination with the retaining posts 234 and mounting apertures 134, which prevent lateral disengagement of the distal portions 130 and 230, preventing a return to the original open position.

As shown in FIG. 8, the catheter patch assembly 300 may be formed to be associated with the distal portion 130, 230 of the upper arm 110 and the lower arm 210. The catheter patch assembly 300 may include a tacky layer 320 and a release liner 330. The catheter patch assembly 300 may also include an upper, structural layer, preferably formed from a material such as a high moisture-vapor transmission (MVTR) polyurethane material, to provide a breathable structural layer for mounting a tacky layer 320. The upper layer preferably allows moisture to be released from the insertion site, but is impermeable to microbial agents. The upper layer may prevent or reduce wrinkling of the tacky layer 320 once applied to the skin, and is suitable for sterile applications common in the pharmaceutical and medical industries, for example.

The tacky layer 320 may be formed of any materials currently in use for catheter patches. Exemplary materials may be found, for example, in U.S. Pat. Nos. 5,569,207, 5,631,322, 6,447,798 and 6,683,120. Preferably, the tacky layer comprises a water soluble polymer, such as a hydrogel. Alternatively or in addition to the aforementioned materials, the catheter patch preferably comprises an antiseptic and/or antimicrobial agent. Suitable antiseptic and/or antimicrobial agents include a chlorhexidine gluconate (CHG) compound, an octenidine compound, an iodine based compound, or other known compounds to increase the effectiveness of the antimicrobial barrier. For example, the tacky layer 320 may include an antiseptic and/or antimicrobial agent on at least a part of a lower surface to facilitate adherence to the skin when the catheter patch is applied around the insertion site of a patient. The antiseptic and/or antimicrobial agent may be applied to cover a significant portion of the lower surface of the tacky layer 320, in particular, substantially the entire patch area surrounding the insertion site.

The lower surface of the catheter patch may be provided with a scrim. The scrim may be composed of any suitable carded non-woven mesh-like material, such as a polypropylene or polyethylene material, for example. The scrim provides additional support to the catheter patch and permits enough of the bottom surface of the catheter patch to contact the skin in order to form an adhesive microbial barrier around the insertion site. During removal of the catheter patch, the scrim may provide structure for lifting the catheter patch away from the skin, enabling a more complete removal of the catheter patch and facilitating an easier cleaning of the area surrounding the insertion site.

As shown also in FIGS. 1 and 2, a release liner 330 may be provided on a lower surface of the tacky layer 320, forming the lower layer of the catheter patch assembly 300. The release liner 330 may be comprised of any material capable of being releasably attached to the tacky layer 320, such as a 125 micron siliconised polyester material, for example, or any suitable material that will protect the catheter patch assembly during transport and storage, and permit easy release from the tacky layer 320 or an adhesive compound provided on the bottom surface of the tacky layer 320. As shown in FIG. 2, the release liner 330 may comprise a tab for gripping and releasing the liner 330 by pulling the tab and peeling the release liner away from the tacky layer 320.

The tacky layer 320 and release liner 330 are preferably assembled in a stacked fashion on the distal portion 130 of the upper arm 110. The catheter patch assembly 300 may be introduced onto a lower surface of the distal portion 130 so that the retaining posts 234 extending through the mounting apertures 134 rest adjacent to or optionally contact the catheter patch assembly 300, securing the catheter patch assembly 300 to the applicator assembly 100, preferably via the tacky layer 320. The retaining posts 234 may be formed with additional holding mechanisms 235, such as small ball-ends, for example, having increased diameter over the diameter of the retaining posts (see FIGS. 3 and 5). The holding mechanisms 235 may provide additional support for securing the catheter patch assembly 300 to the applicator assembly 100 while permitting release of the tacky layer 320 when the applicator assembly is used to apply the catheter patch as described below.

As shown in FIG. 1, an access channel 350 may be provided that extends from an aperture 355 to a peripheral edge of the catheter patch assembly 300. The access channel 350 allows the catheter patch and applicator assembly 10, in combination with the positioning notches 132 and 232, to be easily positioned around a percutaneous device during application, preferably without disturbing the device to any significant degree. As shown in FIG. 2, a notch 360, or other suitable guidance feature, may be provided in the tacky layer 320 to further aid in directing the percutaneous device toward the aperture 355 during application.

Another aspect in accordance with the present invention may include providing expansion cross-cut slits 370 that extend in radial directions from the aperture 355. The number, position and radial extension of the individual slits 370 can be varied. The expansion slits 370 allow the catheter patch to easily form fit to a variety of different sized percutaneous devices upon application, ensuring essentially complete coverage and a more effective barrier around the percutaneous device when the catheter patch is applied.

Figure 9:
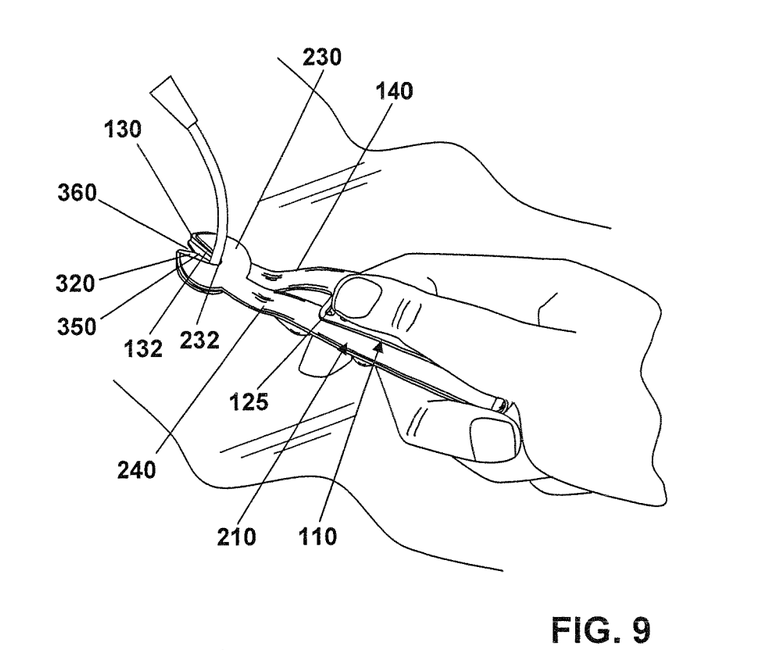
FIG. 9 is an additional perspective view of the catheter patch and applicator assembly of FIG. 1, in accordance with certain aspects of the present invention.

As shown in FIGS. 6-8, the applicator assembly 100 may be provided with features for enhanced ergonomic handling of the assembly and increased dexterity during application of the catheter patch. Raised ridges 125, for example, may be provided on the base portion 120 of the upper arm 110, and a lateral channel 225 may be formed along the base portion 220 of the lower arm 210. The lateral channel 225 may be defined by a contoured proximal protrusion 226 that extends laterally across the base portion 220 and a contoured distal protrusion 227 that extends laterally across the base portion 220 and forward onto the bridging portion 240, for example, for additional support. Thus, as shown in FIG. 9, the applicator assembly 100 may be held comfortably in the hand of a user, with a thumb naturally placed on the raised ridges 125 for applying downward pressure on the upper arm 110 and with the index finger positioned comfortably in the lateral channel 225 for bracing the applicator assembly 100 against the downward pressure applied by the thumb, for example, and/or for the application of upward pressure on the lower arm 210.

In addition, as illustrated in FIG. 6, the applicator assembly 100 may be formed with an upward sweeping contour from the distal portion 130 to an upper portion of the hinged member 150, providing an elevation distance E from the application surface during use. Thus, when gripped as described above, the fingers of the user are elevated from the application surface so that the catheter patch may be applied without the user contacting the application surface. Moreover, the user's hand and fingers are extended away and shielded from the percutaneous insertion site by the applicator assembly 100, further preventing the likelihood of contamination of a sterilized IV site or the sterilized patch itself by the hands and/or fingers of a user.

In use, with the user holding the applicator assembly 100 with one hand, preferably as described above, the release liner 330 may be disengaged by pulling on the extended tab portion with the other hand, for example, until the liner disengages, exposing a lower surface of the tacky layer 320 of the catheter patch. With a lower surface of the tacky layer 320 of the catheter patch assembly 300 exposed, the applicator assembly 100 may be held above the skin and the percutaneous device positioned within the aperture 355 via the access channel 350 and the positioning notches 132 and 232. Once the percutaneous device is positioned within the aperture 355, the exposed lower surface of the tacky layer 320 is contacted with the skin, preferably to form an adhesive bond essentially entirely around the insertion site of the percutaneous device. The user may exert pressure to form a secure adhesive bond, for example, by pressing on the upper arm 110 with a thumb.

Figure 11:
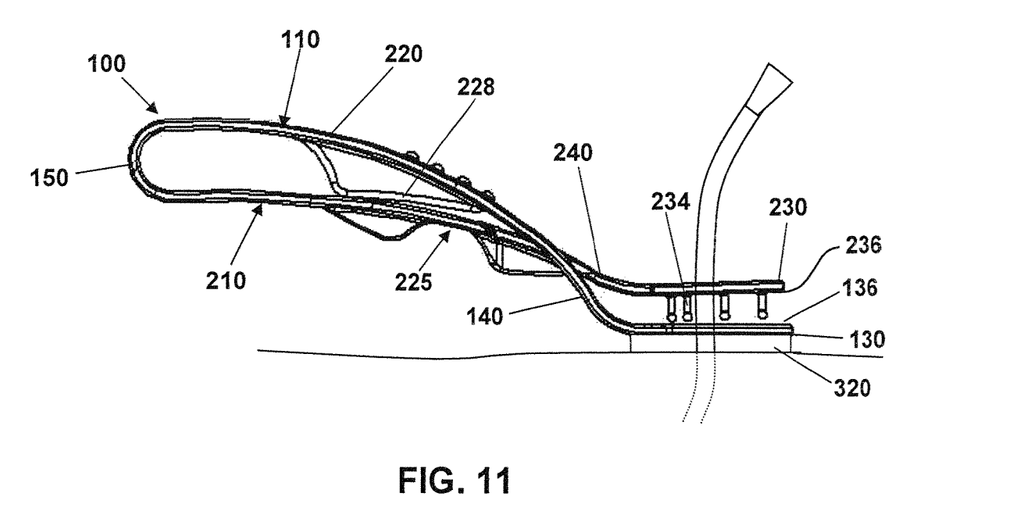
FIG. 11 is a side plan view of the catheter patch and applicator assembly of FIG. 1 in a condition of use, in accordance with certain aspects of the present invention.
Figure 12:
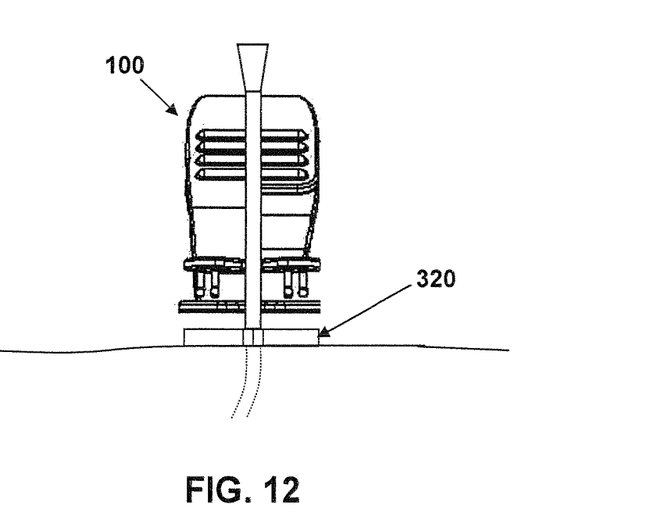
FIG. 12 is a front view of the catheter patch and applicator assembly of FIG. 11, in accordance with certain aspects of the present invention.
Figure 13:
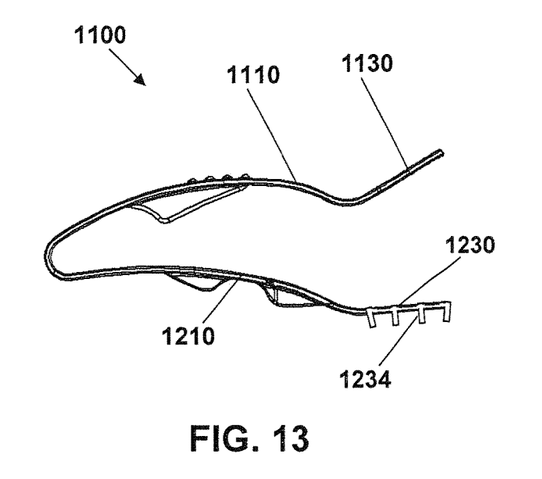
FIG. 13 is a side plan view of an applicator assembly in an initial configuration, in accordance with certain aspects of the present invention.
Figure 14:
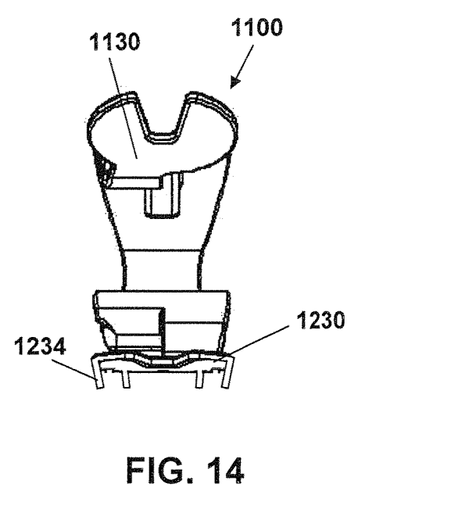
FIG. 14 is a front view of the applicator assembly of FIG. 13, in accordance with certain aspects of the present invention.

With the catheter patch thus applied, and while continuing to exert pressure on the upper arm 110 to hold the catheter patch in place, the user may apply an upward force on the lower arm 210 by applying lateral pressure along the lateral channel 225 with an index finger. As shown in FIGS. 9 and 11, due to the contoured configuration of the applicator assembly 100, and because the bridging portions 140 and 240 extend along opposite sides of the vertical longitudinal centerline plane of the assembly, the bridging portions 140 and 240 may slide past each other unimpeded. Thus, as shown in FIG. 11, while the tacky layer 320 is held firmly in place, the upward pressure applied to the lower arm 210 forces the distal portion 230 to unseat from the distal portion 130, and the retaining posts 234 are disassociated from the catheter patch and exit the mounting apertures 134. A stopper truss 228 may be provided on a lower surface of the upper base portion 220 to provide structural support and prevent breaking of the applicator assembly 100 through the application of excess force, while also preventing the unintentional disengagement of the distal portion 130 from the distal portion 230 during assembly, transport and/or use. In addition, the stopper truss 228 provides an easy gauge for the user in order to determine when the retaining posts 234 are successfully disengaged from the catheter patch. The user simply applies pressure and elevates the lower arm 210 until any further displacement is prevented by the stopper truss 228. As shown in FIG. 12, with the retaining posts 234 disengaged from the catheter patch, and the catheter patch bonded to the skin around the percutaneous insertion site, the user may then raise and safely remove the applicator assembly 100 away from the percutaneous insertion site.

Figure 15:
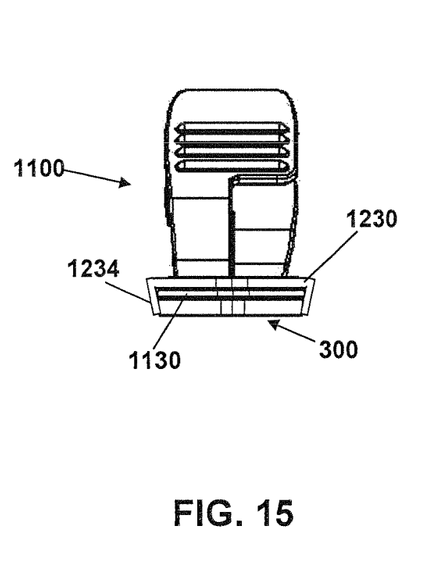
FIG. 15 is a front view of the applicator assembly of FIG. 13 with a catheter patch assembly mounted thereto, in accordance with certain aspects of the present invention.
Figure 16:
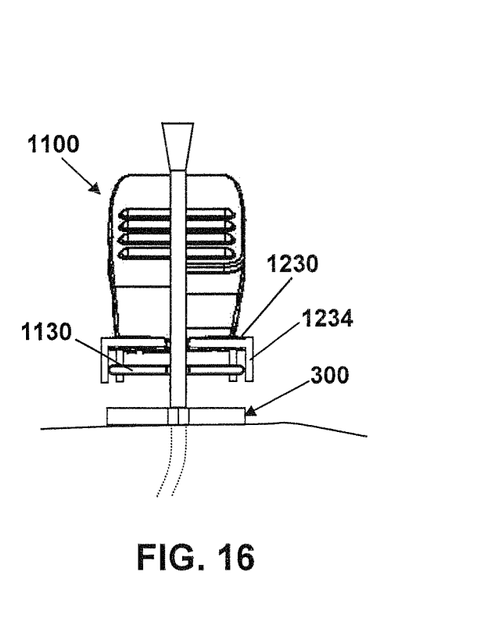
FIG. 16 is a front view of the catheter patch and applicator assembly of FIG. 15 in a condition of use, in accordance with certain aspects of the present invention.

Although the applicator assembly 100 is described above as having distal portions 130 and 230 with mounting apertures 134 that cooperate with retaining posts 234, respectively, a variety of configurations of the distal portions 130 and 230 may provide suitable means for securing a catheter patch assembly 300 to, and releasing a catheter patch assembly 300 from, the applicator assembly 100. For example, FIGS. 13-16 illustrate an applicator assembly 1100 having an upper arm 1110 with a distal portion 1130 and a lower arm 1210 with a distal portion 1230. The applicator assembly 1100 functions in most respects similar to the applicator assembly 100, and, as such, a majority of the structure and functional aspects of the applicator assembly 1100 are not repeated here. The distal portion 1230 may be formed with a set of retaining posts 1234 that extend from a periphery of the distal portion 1230. Rather than extend orthogonally from the distal portion 1230, the retaining posts 1234 may extend at a slight incline from the periphery toward a radial center portion of the distal portion 1230. As shown in FIG. 15, the distal portion 1130 of the upper arm 1110 may be formed with a radial dimension, for example, that is slightly larger than the dimensions of a radial arc defined by the distal tips of the retaining posts 1234. Similarly, the catheter patch assembly 300 may be formed with at least a portion having a radial dimension that is slightly larger than the dimensions of the radial arc defined by the distal tips of the retaining posts 1234. In this manner, when assembled as described above with respect to the applicator 100, the distal portion 1130 of the upper arm 1110 and the catheter patch assembly 300 may be effectively cradled by the retaining posts 1234 until the applicator assembly 1100 is actuated. As shown in FIG. 16, actuation of the applicator assembly 1100 causes the distal portion 1130 to disassociate from the distal portion 1230. The displacement of the distal portion 1130 causes the retaining posts 1234 to be outwardly displaced, releasing the catheter patch assembly 300.

Figure 10:
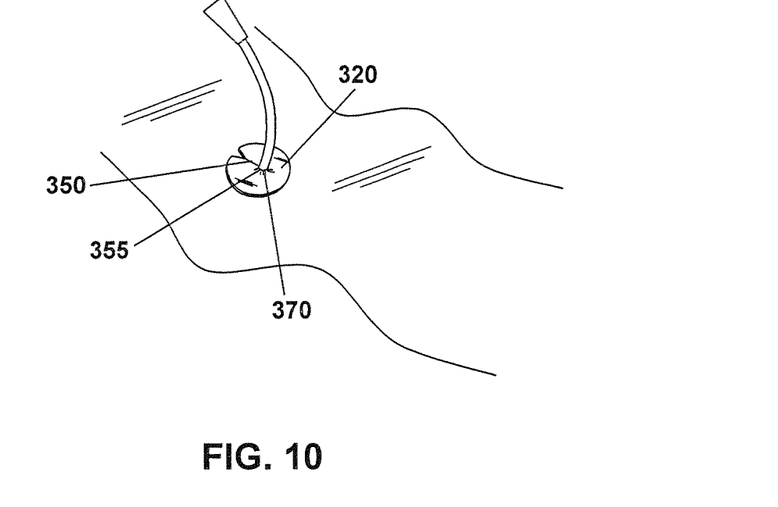
FIG. 10 is a perspective view of a catheter patch as applied to a percutaneous site, in accordance with certain aspects of the present invention.

Application of the catheter patch with one hand enhances the ability of a practitioner to avoid contamination of the insertion site, the catheter patch, and the percutaneous device at or near the insertion site. During application, the fingers and hand of the practitioner are effectively shielded from the insertion site by the applicator assembly 100. As shown in FIG. 10, the aperture 355 preferably form fits to the percutaneous device, allowing the catheter patch to be easily and effectively applied around various sized catheters or other such percutaneous devices. With the catheter patch thus applied, an effective anti-microbial barrier is created by the catheter patch around the insertion site.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly suitable for application of a catheter patch about an insertion site of a percutaneous device, the assembly comprising:
    an upper arm having a proximal end and a distal portion;
    a lower arm having a proximal end and a distal portion;
    a hinge member fixedly joining the proximal ends of the upper arm and the lower arm; and
    a securing mechanism for securing a catheter patch assembly to the applicator assembly, wherein the securing mechanism comprises retaining posts that extend from a lower surface of the lower arm distal portion,
    wherein the securing mechanism extends from the distal portion of the lower arm,
    wherein, in a first position, an upper surface of the upper arm distal portion directly contacts a lower surface of the lower arm distal portion and the securing mechanism extends completely through the upper arm distal portion,
    wherein through-holes are provided in the upper arm distal portion, wherein the retaining posts extend through the through-holes to contact the catheter patch assembly, and
    wherein applying an upward force on the lower arm unseats the lower surface of the lower arm distal portion from the upper surface of the upper arm distal portion and withdraws the securing mechanism from the upper arm distal portion.

2. The applicator assembly of claim 1, further comprising a catheter patch assembly secured against a lower surface of the upper arm distal portion.

3. The applicator assembly of claim 1, wherein the retaining posts disengage from the catheter patch assembly when an applied force displaces the upper arm and the lower arm in a direction toward each other.

4. The applicator assembly of claim 1, wherein the retaining posts extend non-orthogonally from a periphery of the lower arm distal portion.

5. The applicator assembly of claim 4, wherein a radial dimension of the upper arm distal portion is larger than a radial dimension defined by a radial arc between distal tips of the retaining posts.

6. The applicator assembly of claim 2, wherein the catheter patch assembly comprises a tacky layer and a release liner releasably attached to a lower surface of the tacky layer.

7. The applicator assembly of claim 6, wherein the tacky layer comprises a polymer gel.

8. The applicator assembly of claim 6, wherein the tacky layer comprises an aperture and an access channel extending from the aperture to an opening at a frontal portion of the catheter patch.

9. The applicator assembly of claim 8, wherein the tacky layer further comprises at least one expansion slit extending from the aperture.

10. The applicator assembly of claim 9, wherein the tacky layer further comprises a notch provided at a periphery of the access channel.

11. The applicator assembly of claim 1, wherein the upper arm further comprises an upper arm base portion at the proximal end connected to the upper arm distal portion by an upper arm bridging portion.

12. The applicator assembly of claim 11, wherein the upper arm bridging portion is configured to extend longitudinally from the upper arm base portion to the upper arm distal portion along one side of a vertical longitudinal centerline plane of the applicator assembly.

13. The applicator assembly of claim 12, wherein the lower arm further comprises a lower arm base portion at the proximal end connected to the lower arm distal portion by a lower arm bridging portion.

14. The applicator assembly of claim 13, wherein the lower arm bridging portion is configured to extend longitudinally from the lower arm base portion to the lower arm distal portion along the opposite side of a vertical longitudinal centerline plane of the applicator assembly from the side along which the upper arm bridging portion extends.

15. The applicator assembly of claim 1, wherein the hinge member is integrally formed with the upper arm and the lower arm, and wherein the upper arm and the lower arm each extend in a cantilevered manner from the hinge member.

16. The applicator assembly of claim 1, further comprising raised ridges provided on an upper surface of the upper arm for enhanced ergonomic handling of the applicator assembly.

17. The applicator assembly of claim 1, further comprising a lateral channel provided on a lower surface of the lower arm for enhanced ergonomic handling of the applicator assembly.

18. The applicator assembly of claim 1, wherein the applicator assembly is configured with an upward sweeping contour from the upper arm distal portion to an upper portion of the hinged member to provide an elevation distance of the applicator assembly during use.

19. The applicator assembly of claim 1, further comprising a stopper truss on a lower surface of the upper arm that engages the lower arm after a predetermined distance when an applied force displaces the upper arm and the lower arm in a direction toward each other.

20. A method of applying a catheter patch about an insertion site of a percutaneous device, the method comprising:
    providing an applicator assembly comprising an upper arm and a lower arm cantilevered from a hinge member, the upper and lower arms each having distal portions and proximal portions, wherein the applicator assembly is configured with the distal portion of the upper arm positioned below the distal portion of the lower arm, wherein a catheter patch assembly comprising a tacky layer is secured to the applicator assembly, wherein, in a first position, an upper surface of the upper arm distal portion directly contacts a lower surface of the lower arm distal portion and a securing mechanism extends completely through the upper arm distal portion, and wherein the catheter patch assembly is secured toward a lower surface the distal portion of the upper arm by the securing mechanism provided on the distal portion of the lower arm, the securing mechanism comprising retaining posts that extend from a lower surface of the lower arm distal portion;

exposing a lower surface of the tacky layer of the catheter patch assembly;

positioning the percutaneous device within an aperture formed in the tacky layer via an access channel provided in the tacky layer;

contacting the exposed lower surface of the tacky layer with the skin adjacent the percutaneous device insertion site;

applying pressure to the upper arm to hold the tacky layer against the skin; and applying pressure to the lower arm in a direction toward the upper arm to displace the distal portion of the lower arm away from the distal portion of the upper arm and release the tacky layer from the applicator assembly, wherein through-holes are provided in the upper arm distal portion, and wherein the retaining posts extend through the through-holes to contact the catheter patch assembly.

21. The applicator assembly of claim 20, wherein the retaining posts disengage from the catheter patch assembly when an applied force displaces the upper arm and the lower arm in a direction toward each other.

22. The applicator assembly of claim 20, wherein the retaining posts extend non-orthogonally from a periphery of the lower arm distal portion.

23. The applicator assembly of claim 22, wherein a radial dimension of the upper arm distal portion is larger than a radial dimension defined by a radial arc between distal tips of the retaining posts.

24. The applicator assembly of claim 20, wherein the catheter patch assembly comprises a release liner releasably attached to a lower surface of the tacky layer.

25. The applicator assembly of claim 20, wherein the tacky layer comprises a polymer gel.

* * * * *